United States Patent [19]

Delbarre et al.

[11] 4,383,995
[45] May 17, 1983

[54] [4,5] 4H-BENZO [1,2-B] CYCLOHEPTA FURAN DERIVATIVES AND APPLICATION THEREOF AS ANTI-FIBRILLATING AGENTS

[76] Inventors: Bernard Delbarre, Ferme les Carnaux, Ballan Mire, 37300 Joue-les-Tours; Louis Mavoungou-Gomes, 3, rue Desportes, 49000 Angers, both of France

[21] Appl. No.: 318,179

[22] Filed: Nov. 4, 1981

[30] Foreign Application Priority Data

Nov. 10, 1980 [FR] France ................................ 80 23973

[51] Int. Cl.³ ..................... A61K 31/34; C07D 307/93
[52] U.S. Cl. ............................... 424/248.54; 424/250; 424/267; 424/285; 544/153; 544/233; 544/376; 546/196; 549/458
[58] Field of Search ................... 260/346.71; 544/153, 544/233, 376; 546/196; 424/248.54, 250, 267, 285; 549/458

[56] References Cited

U.S. PATENT DOCUMENTS 4,105,785  8/1978  Mauvernay et al. ........... 260/346.71

Primary Examiner—John M. Ford
Assistant Examiner—Bernard Dentz
Attorney, Agent, or Firm—Karl W. Flocks; Sheridan Neimark

[57] ABSTRACT

This invention relates to the derivatives of the following formula:

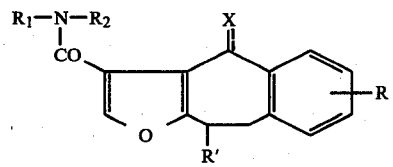

in which R, R', $R_1$, $R_2$ are hydrogen atoms or hydrocarbonated radicals, and X is an oxo, hydroxy, imino or aminal radical.

These compounds have anti-fibrillating activity.

5 Claims, No Drawings

[4,5] 4H-BENZO [1,2-b] CYCLOHEPTA FURAN DERIVATIVES AND APPLICATION THEREOF AS ANTI-FIBRILLATING AGENTS

This invention relates to [4,5]-4H-benzo-[1,2-b]-cyclohepta furane derivatives, a process of preparation and applications thereof, in particular, in therapeutics.

The compounds which are the objects of this invention have the following formula:

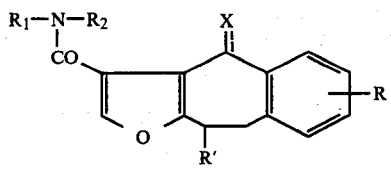

in which R represents a hydrogen atom, an alkyl radical having from 1 to 6 carbon atoms, or an alkoxy radical having from 1 to 6 carbon atoms, R' represents a hydrogen atom, an alkyl radical having from 1 to 6 carbon atoms, a phenyl radical or a phenylalkyl radical, the alkyl part of which has from 1 to 6 carbon atoms, X is a hydroxy radical or an oxo radical and $R_1$ and $R_2$ taken separately represent independently of one another, a hydrogen atom, an alkyl radical having from 1 to 6 carbon atoms, possibly carrying a cyano radical or a radical of the following formula:

in which $R_4$ and $R_5$ represent independently of one another a hydrogen atom, an alkyl radical having from 1 to 6 carbon atoms or form together and with the nitrogen atom to which they are fixed a morpholino radical, and $R_1$ and $R_2$ together form with the nitrogen atom to which they are fixed a morpholino, piperidino or piperazino radical, possibly carrying on the second nitrogen atom, an alkyl radical having from 1 to 6 carbon atoms, or a phenylalkyl radical, the alkyl part of which has from 1 to 6 carbon atoms, or X is an aminal rest

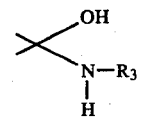

or a radical of the formula $=N-R_3$, $R_3$ representing a hydrogen atom or an alkyl radical having from 1 to 6 carbon atoms, possibly carrying a radical of the following formula

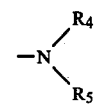

in which $R_4$ and $R_5$ have the same meaning as above, $R_1$ is identical to $R_3$ and $R_2$ is a hydrogen atom, or X forms with $R_2$ a bridge $=N-$ and $R_1$ represents a hydrogen atom or an alkyl radical having from 1 to 6 carbon atoms, possibly carrying a radical of the following formula:

in which $R_4$ and $R_5$ have the meaning as given above.

This invention also relates to the addition salts of the compounds of formula (I) with acids.

The compounds which are the objects of the present invention can be prepared according to the following reaction scheme:

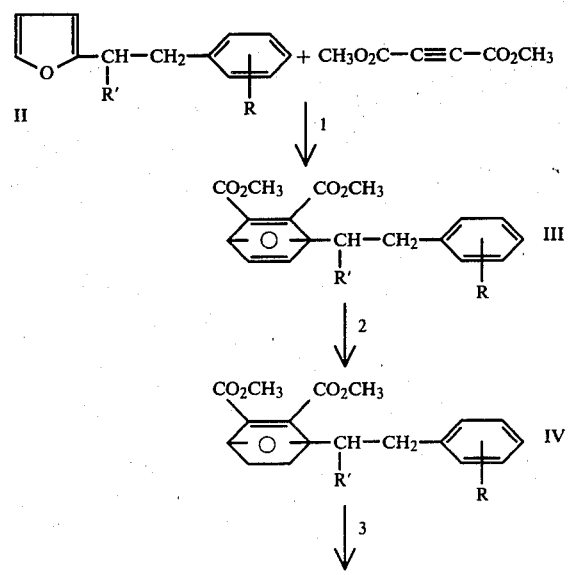

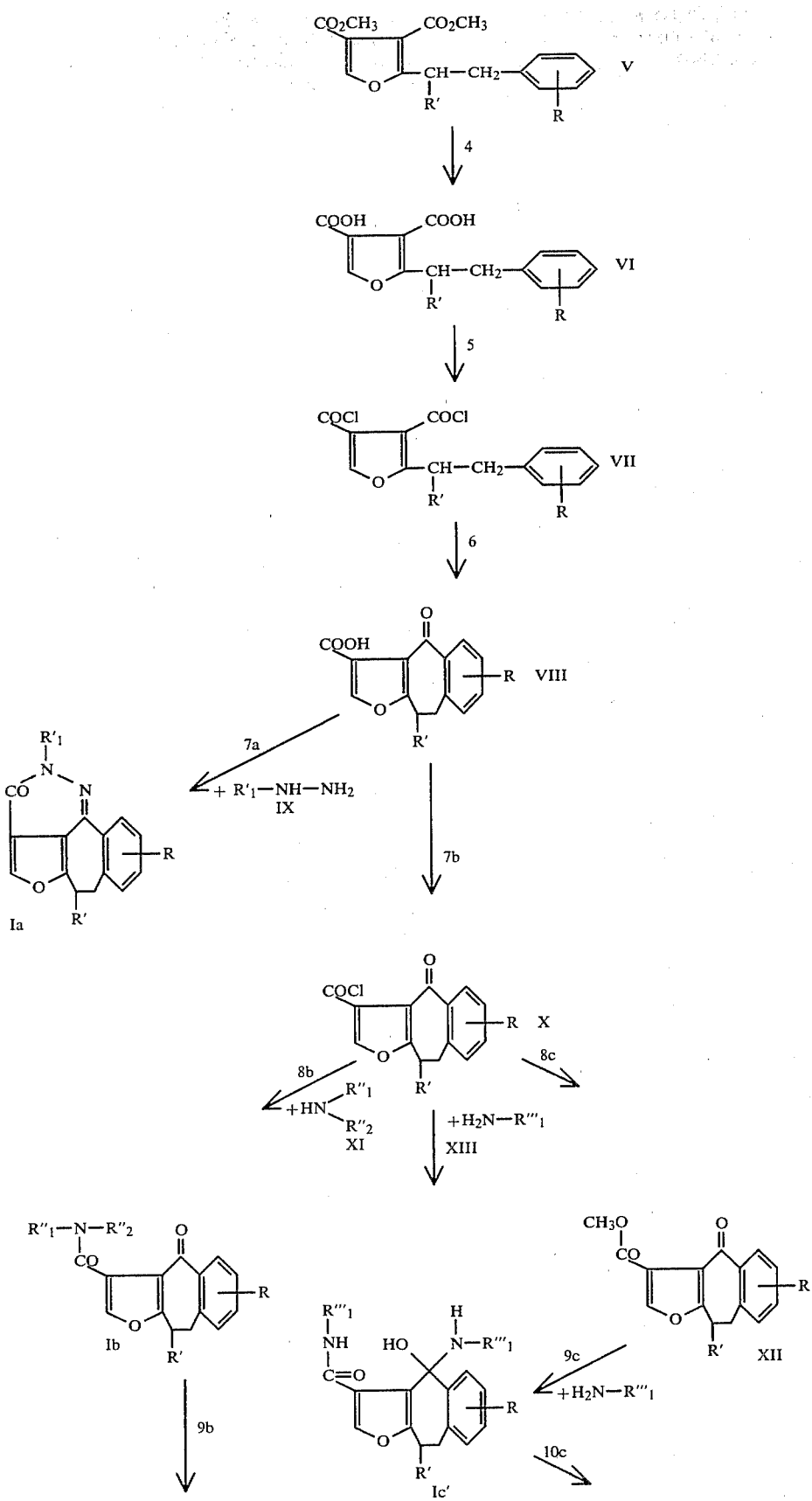

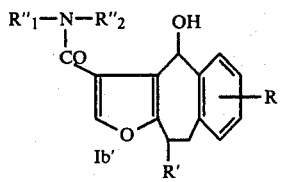

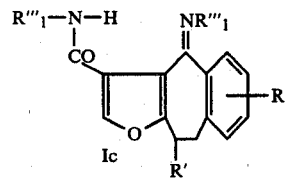

In this scheme, R and R' have the same meaning as in formula (I).

$R'_1$, $R''_1$ and $R'''_2$ as well as $R''_1$ have the meanings given for $R_1$, $R_2$ and $R_3$ respectively, in the cases where X forms with $R_2$ a bridge, X is an oxo or hydroxy group and X is a group

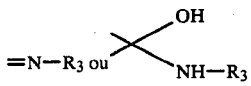

The various stages of synthesis are the following:

Stage 1. Condensation (dienic synthesis) of a (β-aryl)-2-alkylfurane (II) with methyl dicarboxylate acetylene is effected in a solvent such as benzene. A 7-oxa[2,2,1]-bicyclo-2,5-heptadiene (III) derivative, which is not isolated, is obtained.

Stage 2. Partial hydrogenation of the compounds of formula (III) is effected, in particular, in ethanol, in the presence of 10% palladium coal or in ethyl acetate in the presence of Raney nickel. The compound of formula (IV) is obtained.

Stage 3. This compound of formula (IV) is converted directly in accordance with an Alder Rickert's reaction into (β-aryl)-2-alkyl-3,4-dicarbomethoxy-furane (V).

Stage 4. By saponification of diester (V), the corresponding diacid (VI) is obtained.

Stage 5. The diacid is converted to dichloride (VII) by action of thionyl chloride.

Stage 6. Intramolecular cyclization of dichloride (VII) is effected in solution in the carbon sulfide in the presence of aluminum chloride. The aqueous treatment of the reaction product gives a keto-acid of formula (VIII).

Alternatively, the keto-acid (VIII) can also be obtained by direct cyclization of the diacid (VI) in polyphosphoric acid between 100° and 130° C.

Stage 7a. The treatment of the keto-acid (VIII) by a hydrazine (IX) leads to a compound of formula (I) in which X forms with $R_2$ a bridge =N— (formula Ia).

Stage 7b. The treatment of the keto-acid (VIII) by the thionyl chloride leads to the acid chloride (X).

Stage 8b. The treatment of the acid chloride (X) by an amine (XI) leads to a compound of formula (I) in which X is an oxo radical (formula Ib).

Stage 9b. The reduction of the compound (Ib) by BH$_4$K leads to a compound of formula (I) in which X is an hydroxy radical (formula I'b).

Stage 8c. The treatment of the acid chloride (X) by methanol leads to ester (XII).

Stage 9c. The treatment of ester (XII) by an amine (XIII) leads to the compound (Ic'); this product can also be obtained by treating the acid chloride (XI) by amine (XIII) in excess. The derivative (Ic') leads by dehydration to the compound of formula (I) in which X is a radical =N—R$_3$ (formula Ic) (stage 10c).

Some of the compounds of formula (II) used as the starting material for synthesizing compounds of formula (I) are known (Freund, Immerwahr Ber. 1890, 23, 2847 and R. B. Woodward J. Amer. Chem. Soc. 1940, 62, 1478).

The preparation processes described, however, have not given satisfactory results. Therefore, these compounds have been prepared according to a unique process according to the following reaction scheme:

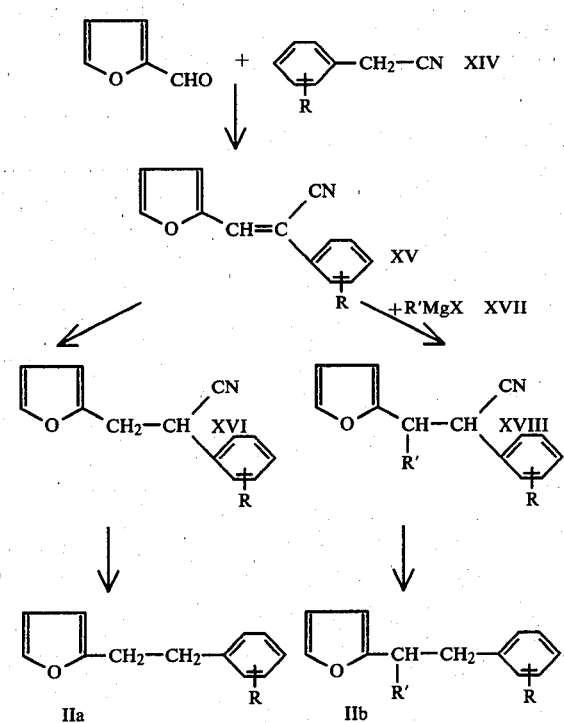

This process consists of first condensing furfural with an arylacetonitrile (XIV) in the presence of sodium ethylate.

Thus, there is obtained a 2-aryl-3-(α-furyl)-propenenitrile (XV) with a good yield.

To prepare the compounds of formula (II), in which R' is a hydrogen atom (formula IIa), hydrogenation is effected by means of potassium borohydride in hydroalcoholic solution. The saturated nitrile so obtained (XVI) is then submitted to a reductive scission by sodium and ethanol. To prepare the compounds of formula (II) in which R' is different from hydrogen (formula IIb) there is effected an addition of the organomagnesium (XVII) onto the nitrile (XV) and the so obtained saturated nitrile is submitted to a reductive scission by sodium and ethanol.

The following examples illustrate the preparation of the compounds in accordance with the invention.

A. PREPARATION OF THE STARTING COMPOUNDS.

(a) 2-phenyl-3-(α-furyl)-propenenitrile.

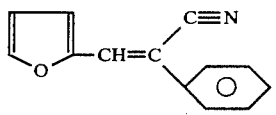

In a six-liter flask provided with a mechanical agitator, a drop funnel and a refrigerant, 5 moles of freshly distilled furfural and 5.10 moles of benzyl cyanide are introduced. The flask being cooled down on ice, under agitation, there is added by the drop funnel an ethanolic solution of sodium ethylate prepared from 23 g of sodium and 400 cm³ of pure ethanol. The reaction is exothermic. Five minutes after addition of ethylate 65 g of acetic acid, 2.5 liters of benzene and 1 liter of water are added. The organic phase is decanted, washed in water and dried on sodium sulphate. After elimination of benzene, the residue is distilled under reduced pressure.

Minimum yield: 95%
Boiling point/15 mm Hg: 190°–195° C.
Melting point: 41°–42° C.
Yellowish crystals darkening in air.
(b) 2-phenyl-3-(α-furyl)-propanenitrile.

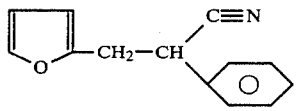

In a two-liter, three-necked flask provided with a mechanical agitator and a refrigerant, 200 g of 2-phenyl-3-(α-furyl)-propenenitrile are dissolved hot in 300 cm³ of absolute ethanol. To the cooled solution there is added 30 g of finely pulverized potassium borohydride, then 100 cm³ of water. The mixture is brought to reflux for 7 hours, then left for 12 hours at the room temperature. After acidification by 50 cm³ of acetic acid, the ethanol is distilled. The residue is separated into two layers. There is extracted by benzene (500 cm³). The benzenic solution is washed in water, dried on sodium sulphate. After elimination of benzene, the saturated nitrile is distilled under reduced pressure.

Yield: 170 g, 85%
Boiling point/13 mm Hg: 167°–168° C.
$n_{D19}^{20}$: 1.5444
$d_4$: 1.090
(c) 2-phenethyl-furane.

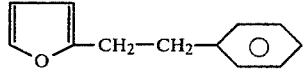

In a two-liter, three-necked flask provided with an agitator, a refrigerant and a drop funnel, 37 g of sodium are dispersed hot in 175 cm³ of boiling toluene. The heating being stopped, and the agitation maintained, there is added by the drop funnel, 0.25 mole of 2-phenyl-3-(α-furyl)-propanenitrile mixed with 40 cm³ of absolute ethanol. The addition is adjusted to maintain a self-supported reflux of the reaction mixture. Ethanol is added dropwise to destroy the excess of sodium. The mixture is then cooled, treated with one liter of water. It separates into two layers. The organic layer is separated; the aqueous layer is saturated with sodium chloride and extracted with toluene (400 cm³). The organic solutions are mixed, washed with water and dried on sodium sulphate. After distillation of toluene the residue is stripped under reduced pressure.

Yield: 90%
Boiling point/10 mm Hg: 112° C.
$n_{D19}^{19}$: 1.5385
$d_4$: 1.023.

The characteristics of the compounds of formula(II) prepared by reductive scission of the corresponding saturated nitriles are set out below.

| R | R' | B.p. mm | $n_D^{19}$ | $d_4^{19}$ | Y. % | Rough formula | C (%) Cal. | C (%) f. | H (%) Cal. | H (%) f. |
|---|---|---|---|---|---|---|---|---|---|---|
| H | H | 112°10 | 1.5385 | 1.023 | 90 | $C_{12}H_{12}O$ | 83.73 | 83.70 | 6.97 | 7.1 |
| H | $CH_3$ | 116°12 | 1.5315 | 1.005 | 88 | $C_{13}H_{14}O$ | 83.88 | 83.80 | 7.52 | 7.1 |
| H | $C_2H_5$ | 125°11 | 1.5247 | 0.995 | 90 | $C_{14}H_{16}O$ | 84.00 | 83.75 | 8. | 8.3 |
| H | n-$C_3H_7$ | 136°12 | 1.5200 | 0.981 | 85 | $C_{15}H_{18}O$ | 84.12 | 83.90 | 8.39 | 8.5 |
| H | n-$C_4H_9$ | 146°12 | 1.5158 | 0.966 | 83 | $C_{16}H_{20}O$ | 84.22 | 83.90 | 8.77 | 9.0 |
| H | n-$C_5H_{11}$ | 156°12 | 1.5123 | 0.968 | 85 | $C_{17}H_{22}O$ | 84.31 | 84.30 | 9.08 | 9.1 |
| H | $C_6H_5$ | 191°14 | 1.5780 | 1.074 | 80 | $C_{18}H_{16}O$ | 87.10 | 86.50 | 6.44 | 6.4 |
| H | $CH_2$—$C_6H_5$ | 194°12 | 1.5695 | 1.062 | 87 | $C_{19}H_{18}O$ | 87.03 | 87.00 | 6.86 | 7.1 |
| p.$OCH_3$ | H | 156°14 | 1.5420 | 1.074 | 60 | $C_{13}H_{14}O_2$ | 77.24 | 77.25 | 6.92 | 7.0 |

B. PREPARATION OF THE COMPOUNDS IN ACCORDANCE WITH INVENTION (1) 2-phenethyl-3,4-dicarbomethoxy-furane.

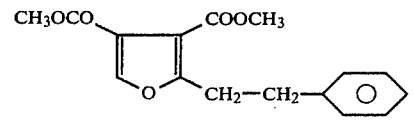

(a) Dienic synthesis

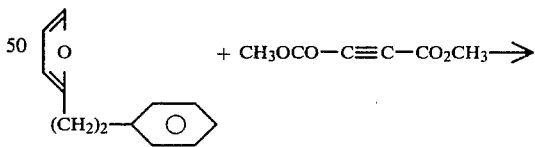

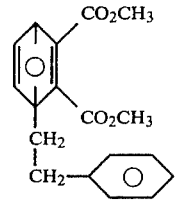

In a one-liter flask, 0.5 mole of 2-phenethyl-furane, 71 g of methyl dicarboxylate acetylene and 120 cm³ of benzene are mixed. The reaction mixture is brought to reflux for 6 hours. After this period, the lacrymogenous nature of acetylic diester has practically disappeared.

The benzene is eliminated under reduced pressure; to the residue from the flask there is added 300 cm³ of ethyl acetate.

(b) Partial hydrogenation when pyrolysis is ended. Then, the residue from the flask is distilled so as to avoid overheating.

The characteristics of the compound so prepared as well as those of other compounds of formula (V) prepared similarly are given in the following table.

| R | R' | B.p. mm | $n_D^{19}$ | $d_4^{19}$ | Y. % | Rough formula | C (%) Cal. | f. | H (%) Cal. | f. |
|---|----|---------|------------|------------|------|---------------|------------|------|------------|------|
| H | H | 212°12 | 1.5335 | 1.179 | 91 | $C_{16}H_{16}O_5$ | 66.68 | 66.60 | 5.55 | 5.60 |
| H | $CH_3$ | 219°19 | 1.5290 | 1.160 | 84 | $C_{17}H_{18}O_5$ | 67.55 | 67.10 | 5.96 | 6.55 |
| H | $C_2H_5$ | 221°19 | 1.5250 | 1.153 | 83 | $C_{18}H_{20}O_5$ | 68.35 | 67.90 | 6.33 | 6.45 |
| p.OCH₃ | H | 250°20 | 1.5370 | 1.204 | 88 | $C_{17}H_{18}O_6$ | 64.15 | 63.30 | 5.66 | 5.70 |

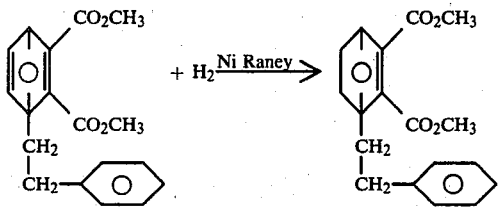

The solution in ethyl acetate obtained in the preceding stage is hydrogenated in the presence of 10 g of Raney nickel previously washed in water (three times), in ethanol (three times), and ethyl acetate (three times), such rigorous washing permitting better dispersion of the catalyst in the solvent used. The reaction is exothermic and lasts at most 45 minutes to 1 hour (fixation of 11.2 to 11.4 liters of hydrogen). The solution is filtered; the filtrate is evaporated under reduced pressure. The viscous and brownish residue is introduced into a Vigreux flask of 250 cm³ mounted for effecting distillation under reduced pressure (capillary tube, thermometer).

(c) Pyrolysis

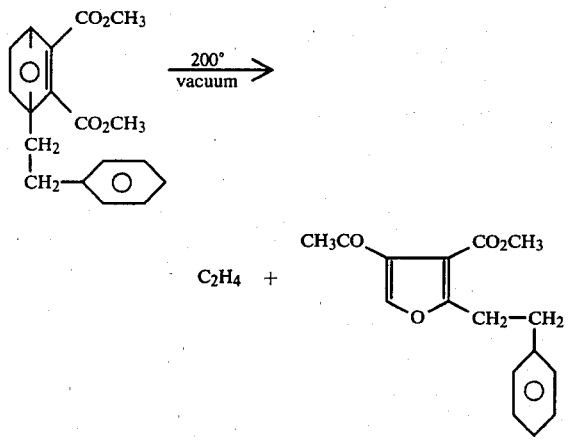

The previous flask is connected to a refrigerant, a separator and to a vacuum water blast pump; the initial pressure is from 12 to 15 mm of mercury. In the heating thermolysis of the partial hydrogenate releases ethylene which is eliminated in the water blast pump; the inner pressure increases and returns to its initial value only (2) 2-phenethyl-3,4-dicarboxy-furane.

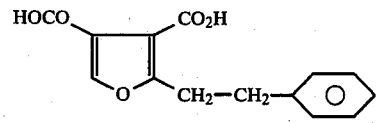

A mixture of 0.2 M of 2-phenethyl-3,4-dicarbomethoxyfurane, 56 g of potash, 200 cm³ of ethanol and 70 cm³ of water is brought to reflux for 5 hours. Ethanol is then distilled at normal pressure. The residue is mixed with 200 cm³ of water, cooled and poured on 100 cm³ of pure hydrochloric acid (about 12 N). The precipitate is washed in water, dried. It is recrystallized in the ethanol/water mixture.

The characteristics of the compound so prepared as well as those of other compounds of formula (VI) prepared similarly are given in the following table.

| R | R' | Melt. °C. | Yield % | Rough formula | C % Cal. | found | H % Cal. | found |
|---|----|-----------|---------|---------------|----------|-------|----------|-------|
| H | H | 148° | 98 | $C_{14}H_{12}O_5$ | 64.61 | 65.05 | 4.61 | 4.63 |
| H | $CH_3$ | 207° | 98 | $C_{15}H_{14}O_5$ | 65.70 | 65.35 | 5.10 | 4.95 |
| H | $C_2H_5$ | 167° | 98 | $C_{16}H_{16}O_5$ | 66.66 | 66.00 | 5.55 | 5.25 |
| p.OCH₃ | H | 165° | 97 | $C_{15}H_{14}O_6$ | 62.07 | 62.20 | 4.82 | 4.73 |

(3) 3-carboxy-4-one-[4,5]-4H-benzo-[1,2-b]-cycloheptafurane

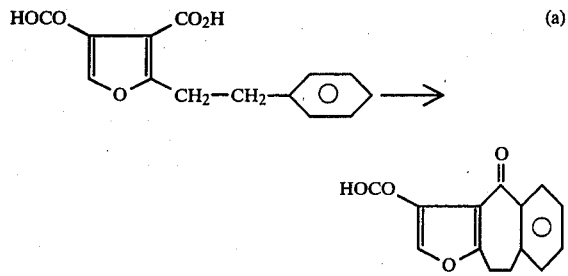

26 g of raw and dry 2-phenethyl-3,4-dicarboxy-furane are finely pulverized and mixed with 200 g of commercial polyphosphoric acid. The mixture is stirred and heated for 30 to 40 minutes between 100° and 130° C. After this period, the reaction mixture is poured under agitation in a flask containing 700 cm³ of water. The crystalline precipitate obtained is filtered, washed in water and recrystallized in chloroform after coal decolorization.

Yield: 19.5 g, 80%

Melting point: 174° C.

(b) Alternate process

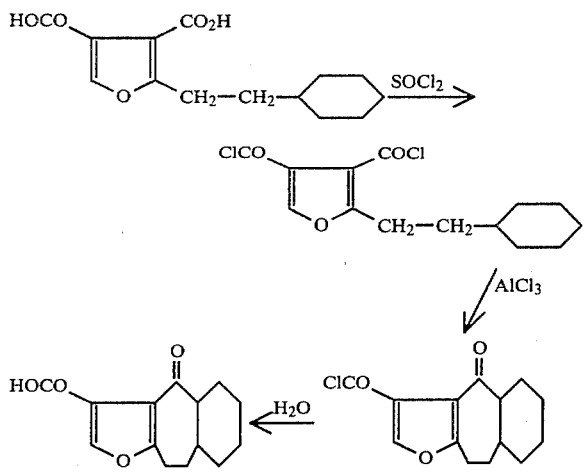

A mixture of 0.25 M of 2-phenethyl-3,4-dicarboxy-furane, 120 g of thionyl chloride is brought to reflux for 3 hours. The excess of thionyl chloride is eliminated under vacuum and the residue of raw furanic acid dichloride is diluted in 250 cm³ of carbon sulphide.

In a one-liter, three-necked flask provided with a mechanical agitator, a refrigerant and a drop funnel there are introduced 75 g of aluminum chloride and 600 cm³ of carbon sulphide. The mixture is brought to reflux during the dropwise addition of the sulfocarbonic solution of furanic acid dichloride. Reflux is maintained for 2 hours after total addition. After this period, release of hydrochloric acid is practically ended. At rest, the reaction mixture separates into two layers. The liquid layer is decanted, washed in water and dried on sodium sulphate. After distillation of carbon sulphide about 3 g of the expected ketonic acid are collected. The solid layer is decomposed by ice (1 kg), the reaction being very strong and accompanied with vapours of carbon sulphide and hydrochloric acid. After decomposition, alumina is solubilized by addition of 100 cm³ of hydrochloric acid. The precipitate is filtered, washed in water and dried. It is recrystallized in chloroform after coal decolorization.

The characteristics of the compound so prepared as well as those of other compounds of formula (VIII) prepared similarly are given in the following table.

| R | M.p. °C. | Yield % | Rough formula | C % Calc. | C % found | H % Calc. | H % found |
|---|---|---|---|---|---|---|---|
| H | 174 | 85 | C₁₄H₁₀O₄ | 69.42 | 69.50 | 4.13 | 4.20 |
| CH₃ | 127 | 55 | C₁₅H₁₂O₄ | 70.31 | 70.00 | 4.68 | 4.40 |
| C₂H₅ | 107 | 50 | C₁₆H₁₄O₄ | 71.11 | 70.40 | 5.18 | 5.00 |

(4) 3-chlorocarbonyl-4-one-[4,5]-4H-benzo-[1,2-b]-cycloheptafurane

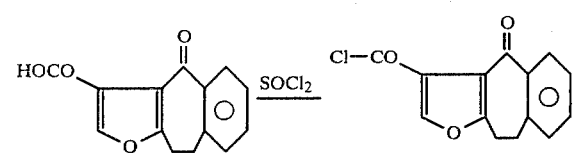

There is brought to reflux for 4 hours a mixture of 70 g of 3-carboxy-4-one-[4,5]-4H-benzo-[1,2-b]-cyclohepta-furane, 90 g of thionyl chloride and 110 cm³ of toluene. The solvent and the reactive in excess are evaporated under vacuum. The residue is mixed hot with 120 cm³ of toluene and decolored on coal. It is filtered. The filtrate added to 30 cm³ of petroleum ether is cooled on ice. A first croc of 65 g of whitish crystals is collected.
Yield: 86.3%
Melting point: 92° C.

(5) 3-carbomethoxy-4-one-[4,5]-4H-benzo-[1,2-b]-cyclohepta-furane

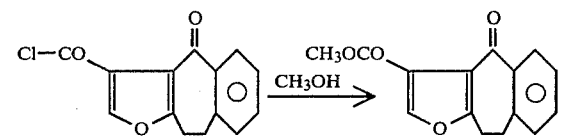

There is brought to reflux for 15 hours a mixture of 0.1 M of ketonic acid chloride and 200 cm³ of methanol. (The reaction can be accelerated by addition of 15 cm³ of pyridine). Methanol is then distilled. The residue is mixed with 100 cm³ of benzene washed in water in a solution saturated with sodium bicarbonate and then again washed in water. After drying on sodium sulfate and elimination of benzene, it is stripped under reduced pressure.
Yield: 85 to 90%
Boiling point/16 mm Hg: 244° C.
Melting point: 53° C.

(6) Diethylamino-3-carboxamido-diethylamino-4-ethylamino-4-hydroxy-[4,5]-4H-benzo-[1,2-b]-cyclohepta-furane (compound No. 1)

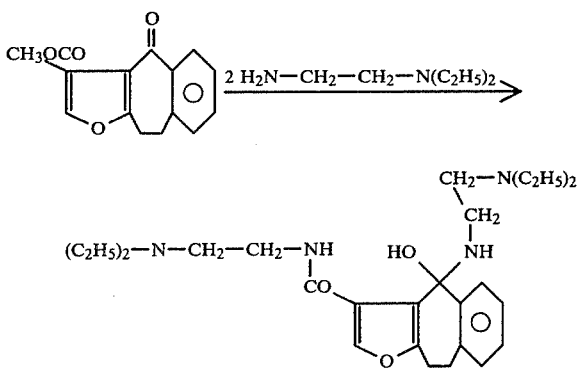

To 25.6 g of ketonic ester (0.10 M), there is added 35 g of commercial N-diethylethylenediamine. The mixture is brought to reflux for 6 hours. The excess of amine is then eliminated under vacuum. The viscous residue is taken up again with 120 cm³ of benzene and decolored on coal. The filtrate is cooled and mixed with 20 cm³ of petroleum ether. 17.5 g of yellowish crystals are collected.
Yield: 40%
Melting point: 133° C.

| Analysis: | C, % | H, % | N, % |
|---|---|---|---|
| Calculated for C₂₆H₄₀N₄O₃ | 68.42 | 8.77 | 12.28 |
| found | 68 | 8.36 | 12.00 |

This derivative can also be obtained by reacting acid chloride with the amine in excess.

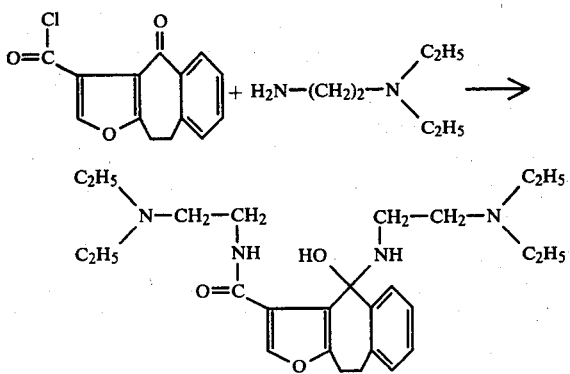

In an Erlenmeyer and under magnetic agitation in a bath of cold water, there is poured 55 ml (0.39 mole) of N,N-diethylethylenediamine and there is added thereto by small portions 20.3 g (0.078 mole) of 3-chlorocarbonyl-4-one-[4,5]-4H-benzo-[1,2-b]-cyclohepta-furane.

It is stirred for 10 hours at the room temperature. After reaction, 100 ml of ethylic ether are added, it is dried and washed in ether. After drying, 19.5 g of cream colored crystals melting at 125°–130° C. (rough yield: 55%) are obtained.

This raw product is dissolved in 100 ml of chloroform, passed on Merck alumina, activity I, brought to dry state, and recrystallized in acetone. There is obtained 13.4 g of white crystals melting at 133° C. (yield: 37.5%). $C_{26}H_{40}N_4O_3 = 456.6$.

| Analysis: | C, % | H, % | N, % |
|---|---|---|---|
| Theory | 68.39 | 8.33 | 12.27 |
| found | 68.39 | 8.81 | 12.31 |

(7) Trihydrochloride of diethylamino-3-ethylcarboxamido-diethylamino-4-ethylamino-[4,5]-4H-benzo-[1,2-b]-cyclohepta-furane.

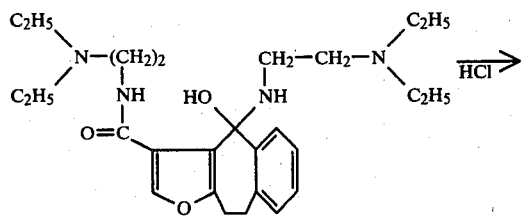

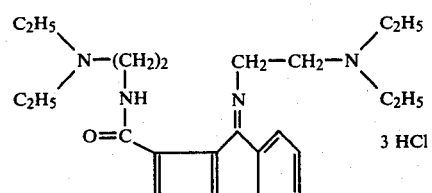

There is stirred at the room temperature for 4 hours 4.56 g of diethylamino-3-ethylcarboxamido-diethylamino-4-ethylamino-4-hydroxy-[4,5]-4H-benzo-[1,2-b]-cyclohepta-furane (0.01 mole), and 50 ml of 1 N HCl (0.05 mole). A limpid light yellow solution is obtained. After reaction, the solvent is removed under vacuum. The oil obtained is dissolved at the room temperature in 150 ml of acetonitrile. This solution is treated by 2 g of carbon-black. It is filtered. 100 ml of solvent are removed under vacuum and it is maintained at 0° C. for 48 hours.

3.36 g of cream colored crystals (hygroscopic product) are dried, (melting point 173° C., yield: 61.5%).

Analysis after drying $C_{26}H_{33}N_4O_2 3HCl = 548$

| | C, % | H, % | N, % | Cl, % |
|---|---|---|---|---|
| Theory | 56.97 | 7.54 | 10.22 | 19.40 |
| found | 56.85 | 7.37 | 10.20 | 19.38 |

(8) Morpholino-2-ethyl-3-oxo-2,3-dihydro-[6,7]-benzo-[1,2,3-c,d]-cyclohepta-[3,4-d]-furo-pyridazine (compound No. 2).

To 8 g of morpholino-ethylhydrazine in 100 cm³ of n-propanol, there is added 12.2 g of keto-acid prepared in 3 (R=R'=H). The mixture is brought to reflux for 4 hours; the propanol is evaporated under reduced pressure. The brown residue is submitted to hot extraction by 500 cm³ of ether. The ether is evaporated. The viscous residue is recrystallized in ethanol after decolorizing on coal.

Yield: 45.6%
Weight: 8 g
Melting point: 135° C.

| Analysis: | C, % | H, % | N, % |
|---|---|---|---|
| calculated for $C_{20}H_{21}N_3O_3$ | 68.37 | 5.98 | 11.96 |
| found | 68 | 5.8 | 11.6 |

(9) 3-oxo-2,3-dihydro-[6,7]-benzo-[1,2,3-c,d]-cyclohepta-[3,4-d]-furo-pyridazine (R=H).

There is brought to reflux for 10 hours a mixture of 2 g of keto-acid prepared in 3, 8 cm³ of hydrated hydrazine and 40 cm³ of acetic acid. The solution is concentrated to 10 cm³ under vacuum and poured in a mixture of 30 cm³ of hydrochloric acid and 100 cm³ of water. The precipitate is washed with water, dried and recrystallized in chloroform. The constants of the products obtained are collected in the following table (R=H).

| Compound | R' | Melt.p. °C. | Rough formula | C % calc. | C % found | H % calc. | H % found | N % calc. | N % found |
|---|---|---|---|---|---|---|---|---|---|
| 3 | H | 258 | $C_{14}H_{10}N_2O_2$ | 70.59 | 70.53 | 4.20 | 4.73 | 11.76 | 11.90 |
| 4 | $CH_3$ | 186 | $C_{15}H_{12}N_2O_2$ | 71.43 | 71.30 | 4.76 | 5.92 | 11.10 | 11.50 |
| 5 | $C_2H_5$ | 173 | $C_{16}H_{14}N_2O_2$ | 72.18 | 71.73 | 5.26 | 5.48 | 10.52 | 11.00 |

(10) (a) 3-carboxamido-4-oxo-[4,5]-4H-benzo-[1,2-b]-cycloheptafurane (R=R'=R₁=R₂=H) (compound No. 6).

To 25 g of raw acid chloride obtained in 4, cooled on ice, there is added cautiously 200 cm³ of previously cooled ammonia. The precipitate is filtered, washed in water and dried. It is recrystallized in acetic acid. Quantitative yield. White crystals. Melting point: 253° C.

| Analysis: | C, % | H, % | N, % |
|---|---|---|---|
| calculated for C$_{14}$H$_{11}$NO$_3$ | 69.71 | 4.56 | 5.81 |
| found | 69.70 | 4.50 | 5.70 |

(b) N-3-alkylcarboxamido-4-oxo-[4,5]-4H-benzo-[1,2b]-cyclohepta-furane (R=R'=H) (compounds No. 7,8,9).

The acid chloride is prepared from 15 g of keto-acid (R=R'=H) and diluted in 50 cm³ of toluene. It is added dropwise to a cold solution of 0.2 M of amine in 125 cm³ of toluene. After 30 minutes of reflux the mixture is washed in water, dried on sodium sulfate, filtered and concentrated under reduced pressure. By addition of ether, there is obtained a yellowish precipitate which is recrystallized in carbon tetrachloride. The yield is quantative.

The constants of the amides are assembled in the following table. (R=R'=H) (compounds No. 3,4,5).

| Compound | R$_1$, R$_2$ | Melt. point °C. | Rough formula | C % calc. | C % found | H % calc. | H % found | N % calc. | N % found |
|---|---|---|---|---|---|---|---|---|---|
| 7 | (C$_2$H$_5$)$_2$ | 118 | C$_{18}$H$_{19}$NO$_3$ | 72.72 | 71.80 | 6.40 | 6.40 | 4.71 | 4.60 |
| 8 | H,n.C$_3$H$_7$ | 112 | C$_{17}$H$_{17}$NO$_3$ | 72.08 | 71.20 | 6.00 | 5.90 | 4.94 | 4.90 |
| 9 | (CH$_2$)$_5$ | 147 | C$_{19}$H$_{19}$NO$_3$ | 73.78 | 72.95 | 6.15 | 6.20 | 4.53 | 4.00 |

Other compounds of the same type are prepared in accordance with the following processing modes:

In a flat bottom Erlenmeyer surmounted by a refrigerant and a drop funnel there is introduced 3 M/100 of ketonic acid chloride (R=R'=H), 30 cm³ of anhydrous tetrahydrofurane. The solution is carried on a heating plate provided with a magnetic agitator. Through the drop funnel there is added a mixture of 3 M/100 of diamine and 10 cm³ of tetrahydrofurane; the precipitation of the hydrochloride is instantaneous. After 5 minutes of reflux, there is cooled on ice; the precipitation is completed by addition of 10 cm³ of anhydrous ether. It is filtered and recrystallized in ethanol. The yields are quantitative.

The melting points are determined on a Maquenne's block.

Compound N° 10

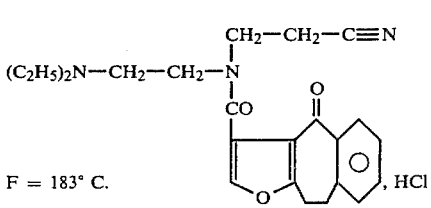

F = 183° C.

Compound N° 11

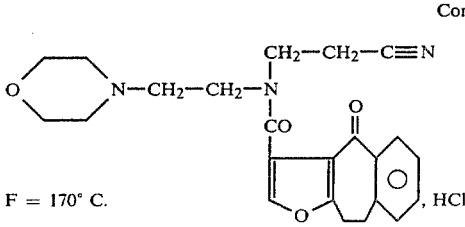

F = 170° C.

Compound N° 12

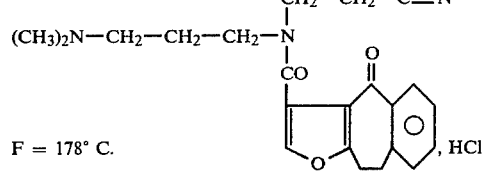

F = 178° C.

Compound N° 13

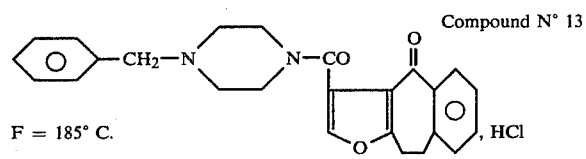

F = 185° C.

(11) 3-piperidinocarbonyl-4-hydroxy-[4,5]-4H-benzo-[1,2-b]-cyclohepta-furane (compound No. 14).

There is brought to reflux for 3 hours a mixture of 10 g of compound No. 9, 3 g of potassium borohydride, 60 cm³ of ethanol and 10 cm³ of water. The solvents are thereafter evaporated under vacuum. The residue taken up by water, provides 9.5 g of white crystals recrystallizable in toluene.

Yield: 95%

Melting point: 158° C.

| Analysis: | C, % | H, % | N, % |
|---|---|---|---|
| calculated for C$_{19}$H$_{21}$NO$_3$ | 73.31 | 6.75 | 4.50 |
| found | 72.60 | 6.60 | 4.45 |

The compounds in accordance with this invention have in particular an antifibrillating activity which proved to be higher than that of procainamide.

We set out below the results of toxocological and pharmaceutical tests.

Table A summarizes the DL$_{50}$ by intraperitoneal and intravenous injections in mice.

TABLE A

| Products | DL 50 (mg/kg) i.p. Gum arabic 10% | i.v. |
|---|---|---|
| Procainamide | 370 | 170 |
| Compound N° 1 | 90 | 24 |
| Compound N° 2 | >1000 | |
| Compound N° 9 | >800 | |
| Compound N° 7 | >800 | |
| Compound N° 3 | >1000 | |
| Compound N° 14 | 500 | |
| Compound N° 10 | | 26.7 |
| Compound N° 11 | | 316.7 |
| Compound N° 12 | | 116 |
| Compound N° 13 | | 20 |

For the hydrosoluble compounds, the activity of the compounds according to the invention was compared to that of procainamide which has been arbitrarily attributed an activity of 1, by two conventional tests, i.e. the test of Dawes (Brit. J. Pharm. 1946 1 90–111) and the method of Somani-Lum (Journal Pharm. Exp. Therap. 1966 147 194–204). The results obtained are set out below in Table B.

TABLE B

| Products | Dawes's test | Somani-Lum's method |
|---|---|---|
| Procainamide | 1 | 1 |
| Compound N° 1 | 13 | 20 |
| Compound N° 10 | 4 | 1 |
| Compound N° 11 | 4 | 5 |
| Compound N° 12 | 4 | 10 |
| Compound N° 13 | 13 | 20 |

For the other compounds the Lawson's method has been used (J. Phar. Exp. Therap. 1968 160 22), the products being administered orally dissolved in gum arabic to a concentration of 10%. The procainamide has also been attributed an activity equal to 1. The results are assembled in Table C hereinbelow.

TABLE C

| Products | Lawson's test |
|---|---|
| Procainamide | 1 |
| Compound N° 1 | 12 |
| Compound N° 2 | 11 |
| Compound N° 9 | 10 |
| Compound N° 7 | 12 |
| Compound N° 3 | 12 |
| Compound N° 14 | 12 |

It results from these tests that the compounds in accordance with the invention have a much more favorable therapeutical indication than procainamide. Moreover, the compounds in accordance with the invention have proved to have an active period much longer than procainamide.

It can be derived from the above that the compounds according to the invention can be used in therapeutics as antifibrillants for the treatment of the cardio-vascular system.

These compounds are administrated in any appropriate form to permit oral or parenteral administration with a dosage involving a quantity of 0.05 to 20 mg/kg of patient per day, in one or more doses.

We claim:

1. A compound of the following formula:

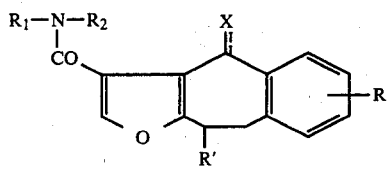

(I)

in which R represents a hydrogen atom, an alkyl radical having from 1 to 6 carbon atoms or an alkoxy radical with from 1 to 6 carbon atoms;

R' represents a hydrogen atom, an alkyl radical having from 1 to 6 carbon atoms, a phenyl radical or a phenylalkyl radical the alkyl part of which has from 1 to 6 carbon atoms, X is a hydroxy radical or an oxo radical, and $R_1$ and $R_2$ taken separately represent independently from one another a hydrogen atom, an alkyl radical having from 1 to 6 carbon atoms, carrying possibly a cyano radical or a radical of the following formula:

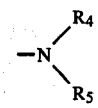

in which $R_4$ and $R_5$ represent independently of one another a hydrogen atom, an alkyl radical having from 1 to 6 carbon atoms or form together and with the nitrogen atom to which they are fixed a morpholino radical, and $R_1$ and $R_2$ together form with the nitrogen atom to which they are fixed a morpholino, piperidino or piperazino radical carrying possibly on the second nitrogen atom an alkyl radical having from 1 to 6 carbon atoms or a phenylalkyl radical the alkyl part of which has from 1 to 6 carbon atoms, or X is a moiety of

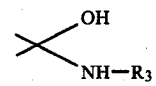

or a radical of formula =N—$R_3$, $R_3$ representing a hydrogen atom or an alkyl radical having from 1 to 6 carbon atoms, possibly carrying a radical of the following formula:

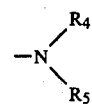

in which $R_4$ and $R_5$ have the same meaning as that given above, $R_1$ is identical to $R_3$, and $R_2$ is a hydrogen atom, or X forms with $R_2$ a bridge =N—, and $R_1$ represents a hydrogen atom or an alkyl radical having from 1 to 6 carbon atoms, possibly carrying a radical of the following formula:

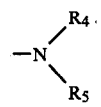

in which $R_4$ and $R_5$ have the same meaning as above, and their addition salts with acids.

2. A compound as claimed in claim 1, which is selected from the group consisting of:
- -diethylamino-3-ethylcarboxamido-diethylamino-4-ethylamino-4-hydroxy-[4,5]-4H-benzo-[1,2-b]-cyclohepta-furane
- -2-morpholino-ethyl-3-oxo-2,3-dihydro-[6,7]-benzo[1,2,3-c,d]-cyclohepta-[3,4-d]-furo-pyridazine,
- -3-oxo-2,3-dihydro-[6,7]-benzo-[1,2,3-c,d]-cyclohepta-[3,4-d]-furo-pyridazine,
- -N,N-3-diethylcarboxyamido-4-oxo-[4,5]-4H-benzo-[1,2-b]-cyclohepta-furane,
- -3-piperidinocarbonyl-4-oxo-[4,5]-4H-benzo-[1,2-b]-cyclohepta-furane,
- -N-(morpholino-ethyl)-N-(2-cyano-ethyl)-3-carboxamido-4-oxo-[4,5]-4H-benzo-[1,2-b]-cyclohepta-furane, -N-(3-dimethylamino propyl)-N-(2-cyano ethyl)-3-carboxamido-4-oxo-[4,5]-4H-benzo-[1,2-b]-cyclohepta-furane, 3-N-(benzyl)-piperazinylcarbonyl-4-oxo-[4,5]-4H-benzo-[1,2-b]-cyclohepta-furane, or 3-piperidino-carbonyl-4-hydroxy-[4,5]-4H-benzo-[1,2-b]-cyclohepta-furane.

3. A composition having antifibrillating activity containing a therapeutically effective amount of a compound of claim 1 or 2 and a pharmaceutically effective carrier.

4. A method of effecting an antifibrillating activity in a mammal in need of said therapy, comprising administering a therapeutically effective amount of a compound of claim 1 or 2 to said mammal.

5. A compound of the following formula:

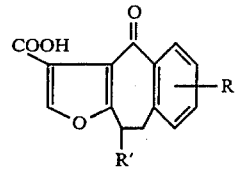

An ester or acid chloride thereof appropriate as an intermediatiary product for the compounds of claim 1, wherein R represents a hydrogen atom, an alkyl radical having from 1 to 6 carbon atoms or an alkoxy radical having from 1 to 6 carbon atoms and R' represents a hydrogen atom, an alkyl radical having from 1 to 6 carbon atoms, a phenyl radical or a phenylalkyl radical the alkyl part of which has from 1 to 6 carbon atoms.

* * * * *